(12) United States Patent
Djeridane

(10) Patent No.: US 9,123,100 B2
(45) Date of Patent: Sep. 1, 2015

(54) METHOD AND SYSTEM FOR PROCESSING MULTIPLE SERIES OF BIOLOGICAL IMAGES OBTAINED FROM A PATIENT

(71) Applicant: OLEA MEDICAL, Gardanne (FR)

(72) Inventor: Faycal Djeridane, Marseilles (FR)

(73) Assignee: OLEA MEDICAL, La Ciotat (FR)

( * ) Notice: Subject to any disclaimer, the term of this patent is extended or adjusted under 35 U.S.C. 154(b) by 0 days.

(21) Appl. No.: 13/666,367

(22) Filed: Nov. 1, 2012

(65) Prior Publication Data

US 2013/0058549 A1 Mar. 7, 2013

Related U.S. Application Data

(63) Continuation of application No. 12/055,751, filed on Mar. 26, 2008, now Pat. No. 8,320,647.
(60) Provisional application No. 60/996,509, filed on Nov. 20, 2007.

(51) Int. Cl.
*A61B 6/00* (2006.01)
*G06T 7/00* (2006.01)
*G06T 7/40* (2006.01)

(52) U.S. Cl.
CPC .............. *G06T 7/0014* (2013.01); *A61B 6/481* (2013.01); *A61B 6/486* (2013.01); *A61B 6/507* (2013.01);
(Continued)

(58) Field of Classification Search
CPC ........ A61B 6/481; A61B 6/486; A61B 6/501; A61B 6/503; A61B 6/504; A61B 6/507; A61B 6/5211; A61B 6/5229; A61B 6/5235; A61B 6/5247
USPC .................................... 324/360–309; 382/128
See application file for complete search history.

(56) References Cited

U.S. PATENT DOCUMENTS 4,335,427 A * 6/1982 Hunt et al. .................... 600/407

4,633,307 A 12/1986 Honda
(Continued)

FOREIGN PATENT DOCUMENTS

| CA | 2 575 313 A1 | 2/2006 |
|---|---|---|
| CN | 1441258 A | 9/2003 |

(Continued)

OTHER PUBLICATIONS

Wataru Kakuda et al., "Optimal definition for PWI/DWI mismatch in acute ischemic stroke patients", Journal of Cerebral Blood Flow & Metabolism (2008), pp. 1-5.
(Continued)

*Primary Examiner* — Thomas R Artman
(74) *Attorney, Agent, or Firm* — Buchanan Ingersoll & Rooney PC

(57) ABSTRACT

A computer-readable storage medium comprising computer-readable program code stored thereon which, when interpreted by a computing apparatus, causes the computing apparatus to implement an image processing tool for processing a plurality of biological images arranged in a plurality of image series wherein certain biological images across different image series have a predefined correspondence with one another. The computer-readable program code comprises computer-readable program code for causing the computing apparatus to: be attentive to receipt of an indication of a selected biological image from the plurality of biological images and belonging to a first one of the image series; be attentive to receipt of an indication of a segmentation mask created based on the selected biological image; apply the segmentation mask to a second biological image from the plurality of biological images, the second biological image belonging to a second one of the image series that is different from the first one of the image series, the second biological image having a predefined correspondence with the selected biological image; and display the second biological image after application of the segmentation mask.

40 Claims, 6 Drawing Sheets

(52) U.S. Cl.
CPC .............. *A61B 6/5229* (2013.01); *G06T 7/403* (2013.01); *G06T 2200/24* (2013.01); *G06T 2207/10016* (2013.01); *G06T 2207/20108* (2013.01); *G06T 2207/30016* (2013.01)

(56) References Cited

U.S. PATENT DOCUMENTS

| | | | |
|---|---|---|---|
| 5,416,415 | A | 5/1995 | Dorri et al. |
| 5,537,491 | A | 7/1996 | Mahoney et al. |
| 5,603,322 | A | 2/1997 | Jesmanowicz et al. |
| 5,647,360 | A * | 7/1997 | Bani-Hashemi et al. ...... 600/425 |
| 5,690,106 | A * | 11/1997 | Bani-Hashemi et al. ...... 600/425 |
| 5,848,121 | A * | 12/1998 | Gupta et al. ..................... 378/62 |
| 5,999,839 | A | 12/1999 | Hardy et al. |
| 6,031,374 | A | 2/2000 | Epstein et al. |
| 6,076,006 | A | 6/2000 | Van Den Brink et al. |
| 6,078,176 | A | 6/2000 | McKinnon |
| 6,154,518 | A * | 11/2000 | Gupta ............................. 378/62 |
| 6,215,848 | B1 | 4/2001 | Linders et al. |
| 6,294,914 | B1 | 9/2001 | Fiat |
| 6,307,368 | B1 | 10/2001 | Vasanawala et al. |
| 6,373,920 | B1 | 4/2002 | Hsieh |
| 6,420,873 | B1 | 7/2002 | Guthrie |
| 6,430,431 | B1 | 8/2002 | De Yoe |
| 6,490,472 | B1 | 12/2002 | Li et al. |
| 6,560,353 | B1 | 5/2003 | Haacke et al. |
| 6,591,128 | B1 | 7/2003 | Wu et al. |
| 6,754,522 | B2 | 6/2004 | Keren |
| 6,757,423 | B1 | 6/2004 | Amini |
| 6,904,163 | B1 | 6/2005 | Fujimura et al. |
| 6,956,373 | B1 | 10/2005 | Brown et al. |
| 6,975,113 | B1 | 12/2005 | Gurr |
| 6,980,845 | B1 | 12/2005 | Alsop |
| 7,215,231 | B1 | 5/2007 | Morrone |
| 7,340,082 | B2 | 3/2008 | Janssen et al. |
| 7,340,290 | B2 | 3/2008 | Deimling |
| 7,545,967 | B1 | 6/2009 | Prince et al. |
| 8,285,014 | B2 * | 10/2012 | Lauritsch et al. ............. 382/128 |
| 8,320,647 | B2 * | 11/2012 | Djeridane ..................... 382/128 |
| 8,588,498 | B2 * | 11/2013 | Novak et al. ................. 382/131 |
| 2001/0007424 | A1 | 7/2001 | Kabasawa et al. |
| 2001/0021794 | A1 | 9/2001 | Muraki et al. |
| 2001/0039377 | A1 * | 11/2001 | Maier et al. ................... 600/410 |
| 2001/0056231 | A1 | 12/2001 | Jesmanowicz et al. |
| 2002/0011842 | A1 | 1/2002 | Fiat |
| 2002/0040718 | A1 | 4/2002 | Ogino |
| 2002/0041283 | A1 | 4/2002 | Saito et al. |
| 2002/0122577 | A1 | 9/2002 | Allouche |
| 2002/0161292 | A1 | 10/2002 | Wintermark et al. |
| 2003/0045791 | A1 | 3/2003 | Carroll |
| 2003/0048935 | A1 * | 3/2003 | Keren ............................. 382/130 |
| 2003/0171671 | A1 | 9/2003 | Miyazaki |
| 2003/0193337 | A1 | 10/2003 | Meyer |
| 2003/0215125 | A1 | 11/2003 | Yakoi et al. |
| 2003/0228043 | A1 | 12/2003 | Ikezaki |
| 2004/0030240 | A1 | 2/2004 | Kimura |
| 2004/0106864 | A1 * | 6/2004 | Rose et al. .................... 600/410 |
| 2004/0113616 | A1 | 6/2004 | Markl et al. |
| 2004/0140804 | A1 | 7/2004 | Polzin et al. |
| 2004/0162482 | A1 | 8/2004 | Assmann et al. |
| 2004/0162483 | A1 | 8/2004 | Kimura |
| 2004/0165758 | A1 | 8/2004 | Furudate et al. |
| 2004/0204644 | A1 | 10/2004 | Tsourarakis et al. |
| 2004/0207401 | A1 | 10/2004 | Kirsch |
| 2004/0218794 | A1 * | 11/2004 | Kao et al. ...................... 382/128 |
| 2005/0007100 | A1 | 1/2005 | Basser et al. |
| 2005/0017716 | A1 | 1/2005 | Fiat |
| 2005/0054913 | A1 | 3/2005 | Duerk et al. |
| 2005/0065428 | A1 | 3/2005 | Keegan et al. |
| 2005/0111719 | A1 | 5/2005 | Pescatore et al. |
| 2005/0127912 | A1 | 6/2005 | Pipe |
| 2005/0154291 | A1 | 7/2005 | Zhao et al. |
| 2005/0165294 | A1 | 7/2005 | Weiss |
| 2005/0171423 | A1 | 8/2005 | Ho et al. |
| 2005/0190955 | A1 | 9/2005 | Brown |
| 2005/0215884 | A1 | 9/2005 | Greicius et al. |
| 2005/0273001 | A1 | 12/2005 | Schmainda et al. |
| 2005/0277828 | A1 | 12/2005 | Alsop |
| 2006/0058630 | A1 | 3/2006 | Harvey |
| 2006/0110018 | A1 | 5/2006 | Chen et al. |
| 2006/0145696 | A1 | 7/2006 | Fuderer et al. |
| 2006/0171578 | A1 | 8/2006 | Novak |
| 2006/0184001 | A1 | 8/2006 | Minkoff et al. |
| 2006/0241382 | A1 | 10/2006 | Li et al. |
| 2007/0014453 | A1 * | 1/2007 | Nowinski et al. ............. 382/128 |
| 2007/0036269 | A1 | 2/2007 | Lienard et al. |
| 2007/0047786 | A1 | 3/2007 | Aklilu et al. |
| 2007/0079253 | A1 | 4/2007 | Leussler |
| 2007/0080689 | A1 | 4/2007 | Konijn et al. |
| 2007/0081713 | A1 | 4/2007 | Jerebko |
| 2007/0085542 | A1 | 4/2007 | Ham et al. |
| 2007/0092120 | A1 | 4/2007 | Guo et al. |
| 2007/0093142 | A1 | 4/2007 | MacDonald et al. |
| 2007/0096736 | A1 | 5/2007 | Kleihorst et al. |
| 2007/0103154 | A1 | 5/2007 | Zhao |
| 2007/0104317 | A1 | 5/2007 | Ohishi |
| 2007/0112264 | A1 | 5/2007 | Wu et al. |
| 2007/0116648 | A1 | 5/2007 | Wong et al. |
| 2007/0120631 | A1 | 5/2007 | Hobbs et al. |
| 2007/0132581 | A1 | 6/2007 | Molyneaux et al. |
| 2007/0134154 | A1 | 6/2007 | Chang et al. |
| 2007/0159169 | A1 | 7/2007 | Sellers |
| 2007/0160277 | A1 | 7/2007 | Slabaugh et al. |
| 2007/0165927 | A1 | 7/2007 | Muradyan et al. |
| 2007/0167736 | A1 | 7/2007 | Dietz et al. |
| 2007/0195932 | A1 * | 8/2007 | Nakaura et al. ............. 378/98.12 |
| 2007/0242069 | A1 | 10/2007 | Matsue et al. |
| 2009/0028409 | A1 | 1/2009 | Tsukagoshi et al. |
| 2009/0034812 | A1 | 2/2009 | Nowinski et al. |
| 2009/0129649 | A1 * | 5/2009 | Djeridane ..................... 382/131 |
| 2013/0058549 | A1 * | 3/2013 | Djeridane ..................... 382/128 |

FOREIGN PATENT DOCUMENTS

| | | |
|---|---|---|
| CN | 1663527 A | 9/2005 |
| CN | 1883386 A | 12/2006 |
| EP | 0 695 948 A1 | 2/1996 |
| EP | 0 997 743 A2 | 5/2000 |
| EP | 1 059 540 A2 | 12/2000 |
| EP | 1 071 367 A1 | 1/2001 |
| EP | 1 094 331 A2 | 4/2001 |
| EP | 1 205 760 A2 | 5/2002 |
| EP | 1 786 475 A2 | 5/2007 |
| EP | 1 788 939 A2 | 5/2007 |
| EP | 1 806 350 A2 | 7/2007 |
| EP | 1 816 485 A2 | 8/2007 |
| GB | 2 315 554 A | 2/1998 |
| GB | 2 345 139 A | 6/2000 |
| GB | 2 356 459 A | 5/2001 |
| GB | 2 431 999 A | 5/2007 |
| GB | 2 433 785 A | 7/2007 |
| GB | 2 434 648 A | 8/2007 |
| JP | 02046828 A2 | 2/1990 |
| JP | 02201903 A2 | 8/1990 |
| JP | 07165617 A | 6/1995 |
| JP | 10323336 A | 12/1998 |
| JP | 11056810 A | 3/1999 |
| JP | 11332847 A | 12/1999 |
| JP | 2003235827 A | 8/2003 |
| JP | 2004097826 A | 4/2004 |
| JP | 2005028139 A | 2/2005 |
| JP | 2006149565 A | 6/2006 |
| JP | 2007068796 A | 3/2007 |
| JP | 2007068798 A | 3/2007 |
| JP | 2007075387 A | 3/2007 |
| KR | 20040097739 A | 11/2004 |
| SG | 0126928 A1 | 11/2006 |
| WO | 97/09690 A1 | 3/1997 |
| WO | 98/47015 A1 | 10/1998 |
| WO | 02/18967 A1 | 3/2002 |
| WO | 02/49512 A2 | 6/2002 |
| WO | 02/069799 A1 | 9/2002 |
| WO | 02/082376 A2 | 10/2002 |
| WO | 02/086530 A1 | 10/2002 |

(56) References Cited

FOREIGN PATENT DOCUMENTS

| WO | 03/015633 | A1 | 2/2003 |
|---|---|---|---|
| WO | 03/044555 | A1 | 5/2003 |
| WO | 03/102618 | A1 | 12/2003 |
| WO | 2004/048993 | A2 | 6/2004 |
| WO | 2004/104611 | A2 | 12/2004 |
| WO | 2005/012926 | A2 | 2/2005 |
| WO | 2005/076030 | A1 | 8/2005 |
| WO | 2005/106522 | A1 | 11/2005 |
| WO | 2005/111649 | A1 | 11/2005 |
| WO | 2006/064091 | A1 | 6/2006 |
| WO | 2006/088453 | A1 | 8/2006 |
| WO | 2006/099011 | A1 | 9/2006 |
| WO | 2006/102370 | A2 | 9/2006 |
| WO | 2006/119085 | A2 | 11/2006 |
| WO | 2006/119164 | A2 | 11/2006 |
| WO | 2006/119259 | A2 | 11/2006 |
| WO | 2006/121967 | A2 | 11/2006 |
| WO | 2006/127687 | A2 | 11/2006 |
| WO | 2007/022499 | A2 | 2/2007 |
| WO | 2007/045076 | A1 | 4/2007 |
| WO | 2007/047915 | A2 | 4/2007 |
| WO | 2007/047981 | A2 | 4/2007 |
| WO | 2007/049166 | A1 | 5/2007 |
| WO | 2007/049167 | A2 | 5/2007 |
| WO | 2007/053507 | A1 | 5/2007 |
| WO | 2007/056961 | A1 | 5/2007 |
| WO | 2007/058632 | A1 | 5/2007 |
| WO | 2007/060950 | A1 | 5/2007 |
| WO | 2007/066250 | A1 | 6/2007 |
| WO | 2007/078405 | A1 | 7/2007 |
| WO | 2007/081730 | A1 | 7/2007 |
| WO | 2007/082495 | A1 | 7/2007 |
| WO | 2007/084442 | A2 | 7/2007 |
| WO | 2007/084747 | A2 | 7/2007 |
| WO | 2007/085342 | A1 | 8/2007 |

OTHER PUBLICATIONS

Gregory W. Albers et al., Magnetic Resonance Imaging Profiles predict Clinical Response to Early Reperfusion: The Defuse Study, Annals of Neuro., vol. 60, No. 5, Nov. 2006, pp. 508-517.

G. Cosnard et al., "Innagerie de diffusion et de perfusion par resonance magnetique de l'encephale", Louvain Med. 118, 1999, pp. 129-140.

Jun Zhang, "Computational Medical Imaging Analysis Chapter 3", Dept. of Computer Science, Univ. of Kentucky, date unknown but believed to be Spring 2007, pp. 1-64.

LightView (TM) Diagnostic Viewer User's Guide, AMICAS Vision (TM) Series, vol. 4, Copyright 2001-2004 AMICAS, Inc., AMICAS Part No. 10-0305, 81 pages.

Rose et al., "MRI Based Diffusion and Perfusion Predictive Model to Estimate Stroke Evolution", Magnetic Resonance Imaging, 19, 2001, pp. 1043-1053.

International Search Report mailed on May 28, 2009 in connection with International patent Application No. PCT/IB2008/001621.

Written opinion of the International Searching Authority mailed on May 28, 2009 in connection with International patent Application No. PCT/IB2008/001621.

James et al., "A supervised method for calculating perfusion/diffusion mismatch volume in . . . ", Computers in Biology and Medicine, vol. 36, No. 11, Nov. 1, 2006, pp. 1268-1287.

* cited by examiner

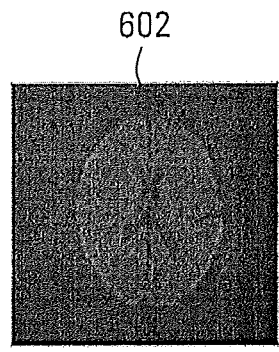
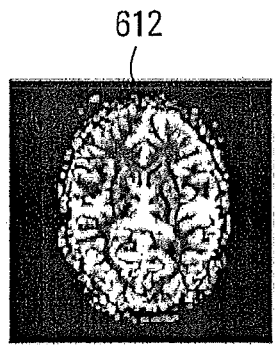
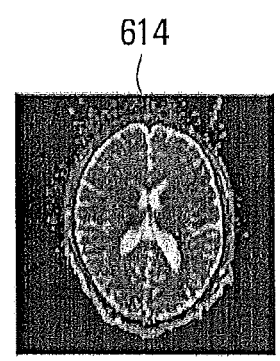
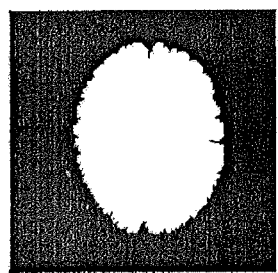
FIG. 6A   FIG. 6B   FIG. 6C

METHOD AND SYSTEM FOR PROCESSING MULTIPLE SERIES OF BIOLOGICAL IMAGES OBTAINED FROM A PATIENT

CROSS-REFERENCE TO RELATED APPLICATION

The present application claims the benefit under 35 USC §119(e) of U.S. provisional patent application Ser. No. 60/996,509 to Fayçal Djeridane, filed on Nov. 20, 2007, hereby Incorporated by reference herein.

FIELD OF THE INVENTION

The present invention relates generally to the processing of biological images and, more particularly, to the processing of multiple series of biological images obtained from a patient affected by an ischemic stroke.

BACKGROUND

Stroke is one of the leading causes of morbidity and mortality in developed countries. A stroke occurs when blood vessels in the brain are compromised. It has been defined as a "sudden neurological shortage presumed to be of vascular origin" (translated from Bousser M G: Classification et orientation générales du diagnostic. In "Accidents vasculaires cérébraux": Bogousslaysky J, Bousser M G, Mas J L, 1993, 95-103, Doin éditeurs.)

There are two main types of stroke, namely hemorrhagic stoke and ischemic stroke. Hemorrhagic stroke is relatively infrequent, and occurs when a blood vessel ruptures, flooding a portion of the brain with blood. On the other hand, ischemic, (or nonhemorrhagic) stroke is much more common and occurs when a blood vessel is blocked (e.g., due to a clot), causing cerebral nervous tissue to be deprived of oxygen, ultimately leading to necrosis if left untreated.

Ischemic stroke is typically treated by administration of a thrombolytic, namely, a drug that aims to dissolve the clot that caused obstruction of the vessel in question. This technique restores blood flow to hypoperfused areas, potentially salvaging those portions of the affected cerebral tissue that have not yet been irreversibly damaged because they have been receiving blood flow from collateral arteries anastomosing with branches of the occluded vascular tree. These portions are known as the "ischemic penumbra", while portions of the cerebral tissue that have been irreversibly damaged due to oxygen deprivation are known as the "core ischemic zone". Further information can be found on the Internet by visiting the Internet Stroke Center at Washington University in St. Louis (http://www.strokecenter.org/education/ais_pathogenesis/22_ischemic_penumbra.htm).

The success of thrombolysis (i.e., treatment with a thrombolytic) therefore relies on rapid administration of the drug to a patient having undergone an ischemic stroke. With cerebral tissue being depleted at a rate of several (approximately 4) million neurons per minute, clinicians find themselves operating within a narrow time window (typically considered to be only a few hours) from occurrence of a stroke if there is to be any hope of success. If a thrombolytic is administered to a patient within this time window, then it may be possible to salvage the ischemic penumbra. However, reperfusion of severely hypoperfused areas can result in hemorrhage with its associated complications. If it turns out that the patient had insignificant salvageable cerebral tissue to begin with (i.e., with dim prospects for a positive outcome from the outset), then administering the thrombolytic will unnecessarily raise the risk of harming the patient.

For these reasons, the decision to administer a thrombolytic is not automatic. Rather, it is made as a function of whether the ischemic penumbra is large enough so as to justify pharmacological treatment and its attendant risk of hemorrhage. Accurate and rapid assessment of this risk/benefit scenario, among other factors, is therefore crucial in the early minutes of treating a patient with stroke symptoms.

As part of the decision making process, clinicians must typically assess the size of the ischemic penumbra and core ischemic zone by viewing and considering numerous images obtained from radiological instruments such as magnetic resonance imaging (MRI) machines. Due to the disparity in image type and presentation, it is only the most highly experienced clinicians who are able to extract useful diagnostic information from these images towards the decision to administer a thrombolytic. However, the number of clinicians having the requisite level of experience is expected to become inadequate to meet the needs of a growing and aging population that naturally brings about an increase in ischemic stroke cases.

As a result, improved image display and processing tools are needed to facilitate the diagnostic process, allowing a broader range of clinicians to assess the costs and benefits of administering a thrombolytic to a patient affected by an ischemic stroke.

SUMMARY OF THE INVENTION

A first broad aspect of the present invention seeks to provide a computer-readable storage medium comprising computer-readable program code stored thereon which, when interpreted by a computing apparatus, causes the computing apparatus to implement an image processing tool for processing a plurality of biological images arranged in a plurality of image series wherein certain biological images across different image series have a predefined correspondence with one another. The computer-readable program code comprises computer-readable program code for causing the computing apparatus to be attentive to receipt of an indication of a selected biological image from the plurality of biological images and belonging to a first one of the image series; computer-readable program code for causing the computing apparatus to be attentive to receipt of an indication of a segmentation mask created based on the selected biological image; computer-readable program code for causing the computing apparatus to apply the segmentation mask to a second biological image from the plurality of biological images, the second biological image belonging to a second one of the image series that is different from the first one of the image series, the second biological image having a predefined correspondence with the selected biological image; and computer-readable program code for causing the computing apparatus to display the second biological image after application of the segmentation mask.

A second broad aspect of the present invention seeks to provide a method, which comprises obtaining a plurality of series of biological images including a first series and a second series, wherein certain ones of the images in the first series and certain ones of the images in the second series are corresponding; creating a respective segmentation mask for each of at least one selected image in the first series; applying each respective segmentation mask to the corresponding image in the second series; and selecting a set of the images in the second series on which to effect a volumetric computation, the selected set of images in the second series including at least one image to which a respective segmentation mask has been applied.

A third broad aspect of the present invention seeks to provide a system, which comprises means for obtaining a plurality of series of biological images including a first series and a second series, wherein certain ones of the images in the first series and certain ones of the images in the second series are corresponding; means for creating a respective segmentation mask for each of at least one selected image in the first series; means for applying each respective segmentation mask to the corresponding image in the second series; and means for selecting a set of the images in the second series on which to effect a volumetric computation, the selected set of images in the second series including at least one image to which a respective segmentation mask has been applied.

A fourth broad aspect of the present invention seeks to provide an image processing system for processing a plurality of biological images arranged in a plurality of image series wherein certain biological images across different image series have a predefined correspondence with one another. The image processing system comprises an input configured to receive an indication of a selected biological image from the plurality of biological images and belonging to a first one of the image series and receive an indication of a segmentation mask created based on the selected biological image; a processing entity configured to apply the segmentation mask to a second biological image from the plurality of biological images, the second biological image belonging to a second one of the image series that is different from the first one of the image series, the second biological image having a predefined correspondence with the selected biological image; and a display entity configured to cause display of the second biological image.

A fifth broad aspect of the present invention seeks to provide a method of processing images that are arranged in a first series of biological images and a second series of biological images, each image being associated with a respective axial slice height. The method comprises:

a) initializing a threshold slice height difference;

b) attempting to identify one or more pairs of corresponding images such that (i) each pair of corresponding images includes one image from each of the first and second series and (ii) the images in each pair are associated with respective slice heights differing by no more than the threshold slice height difference;

c) increasing the threshold slice height difference;

d) repeating steps b) and c) until the threshold slice height difference reaches a maximum threshold slice height difference; and e) for particular images in the first and second series that have been paired further to execution of step b), displaying each particular image in the first series in graphical correspondence with the particular image in the second series to which it is paired.

These and other aspects and features of the present invention will now become apparent to those of ordinary skill in the art upon review of the following description of specific embodiments of the invention in conjunction with the accompanying drawings.

BRIEF DESCRIPTION OF THE DRAWINGS

In the accompanying drawings:

FIGS. 6A through 6C show creation of segmentation masks from respective source images.

It is to be expressly understood that the description and drawings are only for the purpose of illustration of certain embodiments of the invention and are an aid for understanding. They are not intended to be a definition of the limits of the invention.

DETAILED DESCRIPTION

Figure 1:
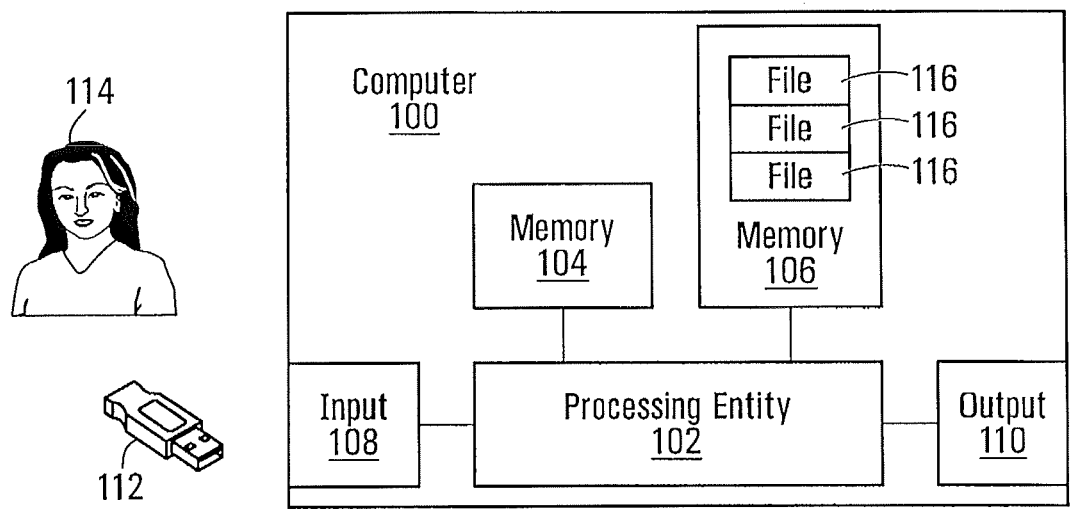
FIG. 1 is a block diagram of a computer that can be configured to implement an image processing method in accordance with a non-limiting embodiment of the present invention.

Non-limiting embodiments of the present invention provide an image processing tool that implements methods of processing biological images. These methods may be performed, at least in part, by a computing apparatus such as a computer shown in FIG. 1 as 100. The computer 100 has a processing entity 102 communicatively coupled to a first memory 104, a second memory 106, an input 108 and an output 110. The processing entity 102 may include one or more processors for processing computer-executable instructions and data. It will be understood by those of ordinary skill in the art that the computer 100 may also include other components not shown in FIG. 1. Also, it should be appreciated that the computer 100 may communicate with other apparatuses and systems (not shown) over a network (not shown). For example, such other apparatuses and systems may include a PACS (picture archiving and communications system) commonly used to store radiological and other biological images of patients in a healthcare setting.

The first memory 104 can be an electronic storage comprising a computer-readable medium storing computer-executable instructions and/or data. The first memory 104 is readily accessible by the processing entity 102 at runtime and may include a volatile memory (e.g., random access memory—RAM) for storing computer-executable instructions and/or data. The second memory 106 can be an electronic storage comprising a computer-readable medium storing computer-executable instructions and/or data. The second memory 106 may include a non-volatile memory (e.g., flash EEPROM) for storing computer-executable instructions and data in a persistent manner. For example, the second memory 106 may store electronic files 116. The files 116 may encode images such as radiological images (specifically, MRI images) and/or other types of biological images of a patient. In some embodiments, the biological images can be two-dimensional and each may comprise a plurality of picture elements (pixels) having respective values. In other embodiments, the biological images can be three-dimensional and each may comprise a plurality of volume elements (voxels) having respective values.

The input 108 may be used to receive commands and other input from a user 114 such as a clinician who is attempting to determine whether to administer a thrombolytic to a patient in real time, or a student who is participating in a simulation exercise. The input 108 may include one or more input devices, examples of which include but are not limited to a keyboard, a mouse, a microphone, a touch screen and an image acquisition apparatus (e.g., a scanner, a camera, an x-ray machine, MRI machine, etc.). The one or more input devices may also include a computer-readable medium such as a removable memory 112 as well as any requisite device for accessing such medium. The one or more input devices may be locally or remotely connected to the processing entity 102, either physically or by way of a communication connection.

The output 110 may include one or more output devices, which may include a display device, such as a screen/monitor. Other examples of output devices include, without limitation, a printer, a speaker, as well as a computer-writable medium and any requisite device for writing to such medium. The one or more output devices may be locally or remotely connected to processing entity 102, either physically or by way of a communication connection.

When the processing entity 102 executes computer-executable instructions stored by one or more of the memories 104, 106, 112, the computer 100 can be caused to carry out one or more of the methods described herein. As can be appreciated, the methods described herein may also be carried out using a hardware device having circuits for performing one or more of the calculations or functions described herein. Other configurations for a computing apparatus are also within the scope of the present invention.

Certain non-limiting embodiments of the present invention have application to diagnosis and treatment of ischemic stroke. In this context, certain classes of biological images are of particular significance. Biological images in a first class are obtained by diffusion-weighted magnetic resonance imaging and are hereinafter referred to as DWI images. DWI images can bring to light a variety of parameters, which include, without limitation;

B0;
B500;
B1000;
ADC (apparent diffusion coefficient);
FLAIR (fluid-attenuated inversion recovery);
T1 (spin-lattice relaxation time);
T2 (spin-spin relaxation time);
Etc.

Biological images in a second class are obtained by perfusion-weighted magnetic resonance imaging and are hereinafter referred to as PWI images. Perfusion is the steady state delivery of blood to tissue parenchyma through the capillaries, representing the microscopic coherent motion of water and cellular material, PWI images can bring to light a variety of hemodynamic parameters, which include, without limitation:

CBV (cerebral blood volume);
CBF (cerebral blood flow);
MTT (mean transit time);
TTP (time to peak);
Etc.

A popular way to perform perfusion MRI is to inject a contrast agent and observe its passage through the brain. Thus, it will be appreciated that PWI images can be obtained by performing computations on a time series of raw images. For information on various non-limiting examples of such computations, and on perfusion MRI generally, reference can be made to the following publications, hereby incorporated by reference herein:

Gregory Sorensen, Peter Reimer: *Cerebral MR Perfusion Imaging, Principles and Current Applications*, Eds. Thieme, 2000; and Wu O, Ostergaard L, Weisskoff R M, Benner T, Rosen B R, Sorensen A G: *Tracer arrival timing-insensitive technique for estimating flow in MR-perfusion-weighted imaging using singular value decomposition with a block-circulant deconvolution matrix, Magn Reson Med.* 2003 July; 50(1): 164-74.

Another hemodynamic parameter that can be brought to light using PWI images is the time to peak of the residue function (sometimes abbreviated "Tmax"), which involves deconvolution of the "tissue concentration over time" curve using an arterial input function from the contralateral middle cerebral artery.

The following references provide additional information regarding the measurement of cerebral blood flow and other parameters.

Ostergaard L, Weisskoff R M, Chesler D A, et al. *High resolution measurement of cerebral blood flow using intravascular tracer bolus passages*, part I: mathematical approach and statistical analysis. *Magn Reson Med* 1996; 36:715-725

Ostergaard L, Sorensen A G, Kwong K K, et al. *High resolution measurement of cerebral blood flow using intravascular tracer bolus passages*, part II: experimental comparison and preliminary results. *Magn Reson Med* 1996; 36:726-736

For the purposes of the description to follow, biological images (including DWI and PWI images) that evidence at least some of the above parameters are assumed to be available to the computer 100 for processing and/or display. Such availability can arise by virtue of the biological images being stored as files 116 in the memory 106 or by the PACS, etc. The set of images that evidences a particular parameter are hereinafter referred to as forming a "series" of images. Thus, there may be plural series of images available for processing and/or display by the computer 100. One or more of the series may include DWI images, while another one or more of the series may include PWI images.

Figure 3:
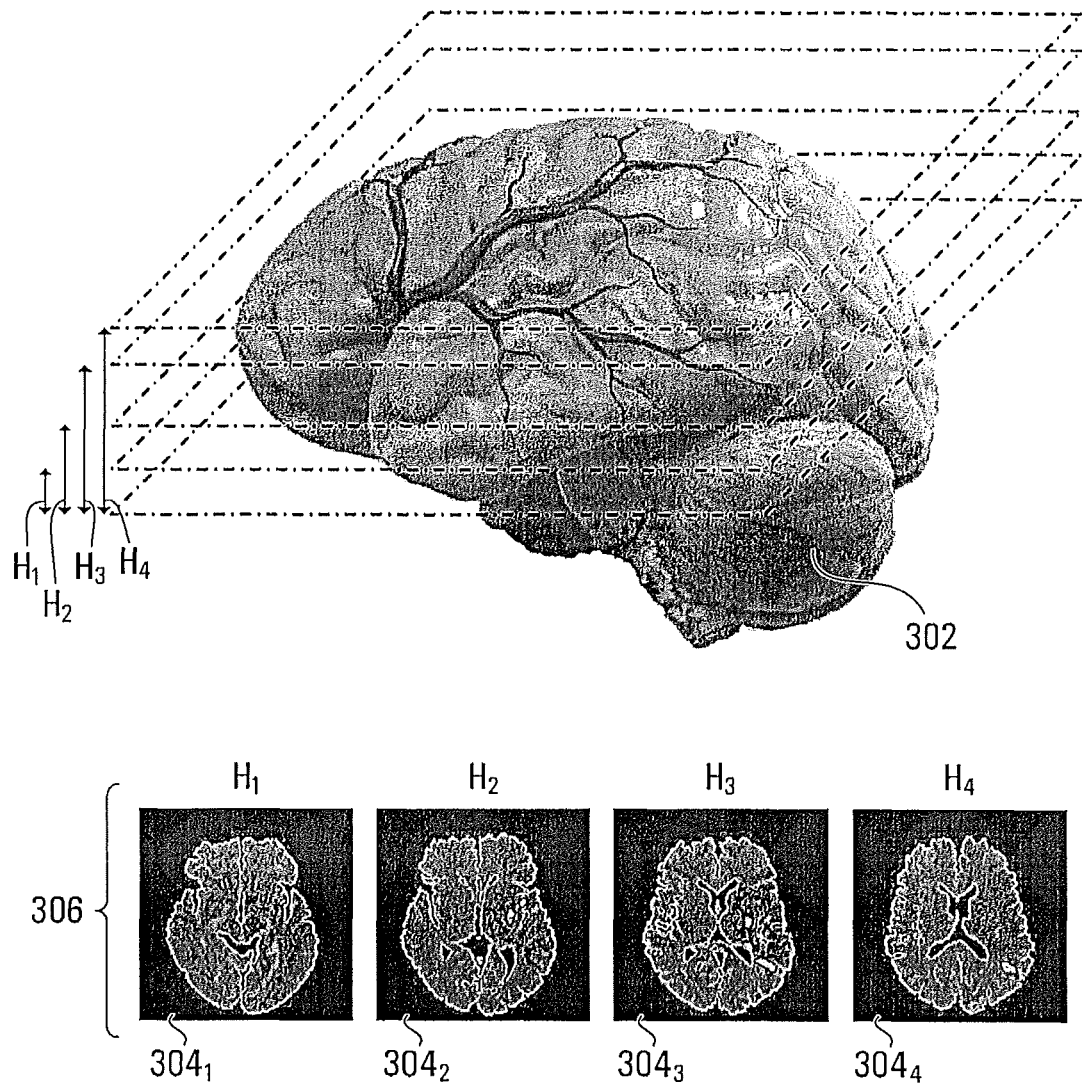
FIG. 3 shows a series of MRI images taken at different axial slice heights.

For the purposes of the description to follow, and with reference to FIG. 3, each biological image $304_1$, $304_2$, $304_3$, $304_4$ in a given series 306 is a two-dimensional axial image of a patient's brain 302 at a particular axial slice height $H_1$, $H_2$, $H_3$, $H_4$. The axial slice height of an image may be indicated in a header portion of a file that encodes the image, such as one of the files 116. A common format for such a file is DICOM (abbreviation of "Digital Imaging and Communications in Medicine"), which includes a DICOM header that specifies the height of the axial slice at which the accompanying image was taken. It should be appreciated that in other embodiments, file formats other than DICOM may be used, including proprietary file formats that may not include a header, whereby the height of an axial slice is recorded in a different fashion. It should also be appreciated that in other applications, views other than axial (e.g., sagittal or coronal) may be of interest.

Figure 2:
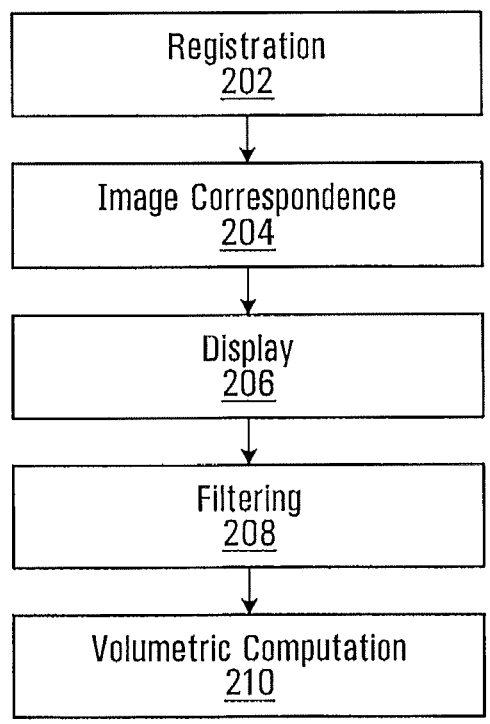
FIG. 2 is a flowchart illustrating steps in an image processing method in accordance with an embodiment of the present invention.

A non-limiting description of an example method that may be performed by the computer 100 when executing computer-readable instructions stored in one or more of the memories 104, 106, 112 is now provided with reference to the flowchart in FIG. 2. Specifically, the method includes the steps of registration 202, image correspondence 204, display 206, filtering 208 and volumetric computation 210. It should be appreciated that not all of these steps are essential in all embodiments. In the description to follow, reference will be made to pixels for reasons of simplicity, with the understanding that reference could also have been made to voxels.

Step 202: Registration

The step of registration 202 generally includes ensuring that all images in all of the series have the same pixel spacing, origin and orientation. This can be achieved using operations of zoom, translation and rotation. Specifically:

a) To achieve the same pixel spacing: consider the non-limiting scenario where each image is associated with a header that indicates the pixel spacing for that image in terms of units of distance. A reference pixel spacing is selected, either automatically by the computer 100 (e.g., as being the median pixel spacing among the various images of the various series) or manually by the user 114 via the input 108. Then, for all images whose pixel spacing is not equal to the reference pixel spacing, an interpolation function (such as, without limitation, the nearest neighbor interpolation function) is applied to those images in order to achieve the reference pixel spacing. Of course, other forms of interpolation and, generally, other methodologies are possible in order to achieve a common pixel spacing without departing from the scope of the present invention.

b) To achieve the same origin: the origin of each image can be a point (e.g., a pixel) that refers to the same physiological structure in each image of each series. The origin can be selected manually by the user 114 via the input 108, although an automatic mechanism can be used without departing from the scope of the present invention. Once the origin has been identified for each image, an absolute origin is selected (namely, the coordinates where the origin will appear for all images once processing is complete), and then it suffices to effect a translation of each image whose origin does not correspond to the absolute origin until such correspondence is achieved.

c) To achieve the same orientation: with all images having the common origin (see b) above), a second reference point (e.g., a pixel) that refers to a second common physiological structure in each image of each series is identified. The second reference point can be selected manually by the user 114 via the input 108, although an automatic mechanism can be used without departing from the scope of the present invention. Once the second reference point has been identified for each image, an absolute reference point is selected (namely, the coordinates where the second reference point will appear for all images once processing is complete), and then it suffices to effect a rotation of each image whose second reference point does not correspond to the absolute reference point until such correspondence is achieved.

Step 204: Image Correspondence

Consider the non-limiting scenario where the images in a particular series are all axial slices taken at different axial slice heights. Consider also that there are multiple series. Then, the step of image correspondence 204 generally includes attempting to identify a group of images, one from each series, that have comparable axial slice heights. The information regarding the axial slice height of a particular image may be available in a header that accompanies the image. An ideal example of two axial slice heights that are comparable includes two axial slice heights that are identical. Thus, an image in series A with a particular axial slice height H, and an image in series B also with an axial slice height H can be said to exhibit image correspondence. However, it is more common to find that images in different series have axial slice heights that are different for each series. In fact, the number of images in each series may itself be different.

Figure 5:
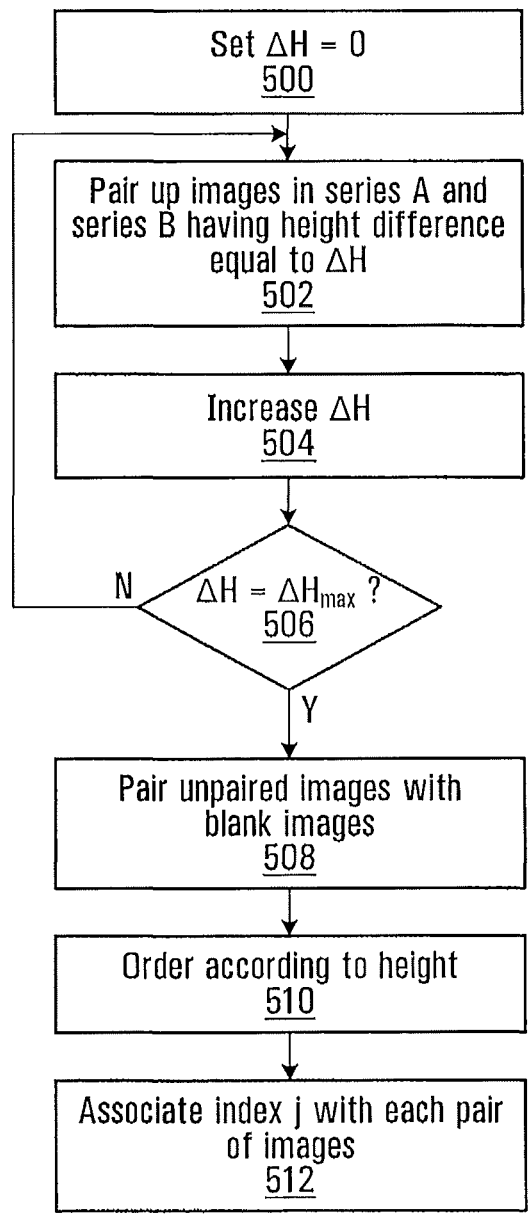
FIG. 5 is a flowchart illustrating steps in establishing correspondence between images in different series as a function of their axial slice heights.

With reference to FIG. 5, one non-limiting methodology for executing the step of image correspondence 204 between pairs of images in two series A and B is as follows (assuming that the various images have already been registered in accordance with the registration step 202). At sub-step 502, select all pairs of images in series A and series B having exactly the same axial slice height (i.e., for which the difference in axial slice height is zero). At sub-step 504, the tolerable axial slice height difference $\Delta H$ is increased (e.g., to one unit of height) and step 502 is repeated. That is to say, from the remaining images in series A and series B, select all pairs of images having an axial slice height that differs only by one unit of height. The tolerable axial slice height difference is increased again at step 504 and the process continues until a maximum tolerable height difference $\Delta H_{max}$ is reached (step 506). The maximum tolerable height difference $\Delta H_{max}$ represents a height difference beyond which two images are simply too distant in the Z-direction (i.e., axially) that they cannot be said to correspond to one another.

At sub-step 508, for any image in series A that was not paired with an image in series B by virtue of step 502, create a blank corresponding B-series image, and for any image in series B that was not paired with an image in series A by virtue of step 502, create a blank corresponding A-series image. At sub-step 510, the images in each series (now potentially including blank images) are ordered in accordance with their axial slice height (or in the case of a blank image, the axial slice height of the corresponding image in the other series). At sub-step 512, an index (e.g., "j") is given to corresponding images in each series. In this way, images denoted A(j) will correspond to images denoted B(j), for any value of j, recalling that the "image" in question may be blank.

Step 206: Display

The step of display 206 generally includes providing a scrolling functionality to view several images in a single series, and/or corresponding images in two or more series simultaneously (such as images A(j) and B(j) for one or more values of j). It is recalled that corresponding images are those images that were found to have a comparable axial slice height.

Figure 4:
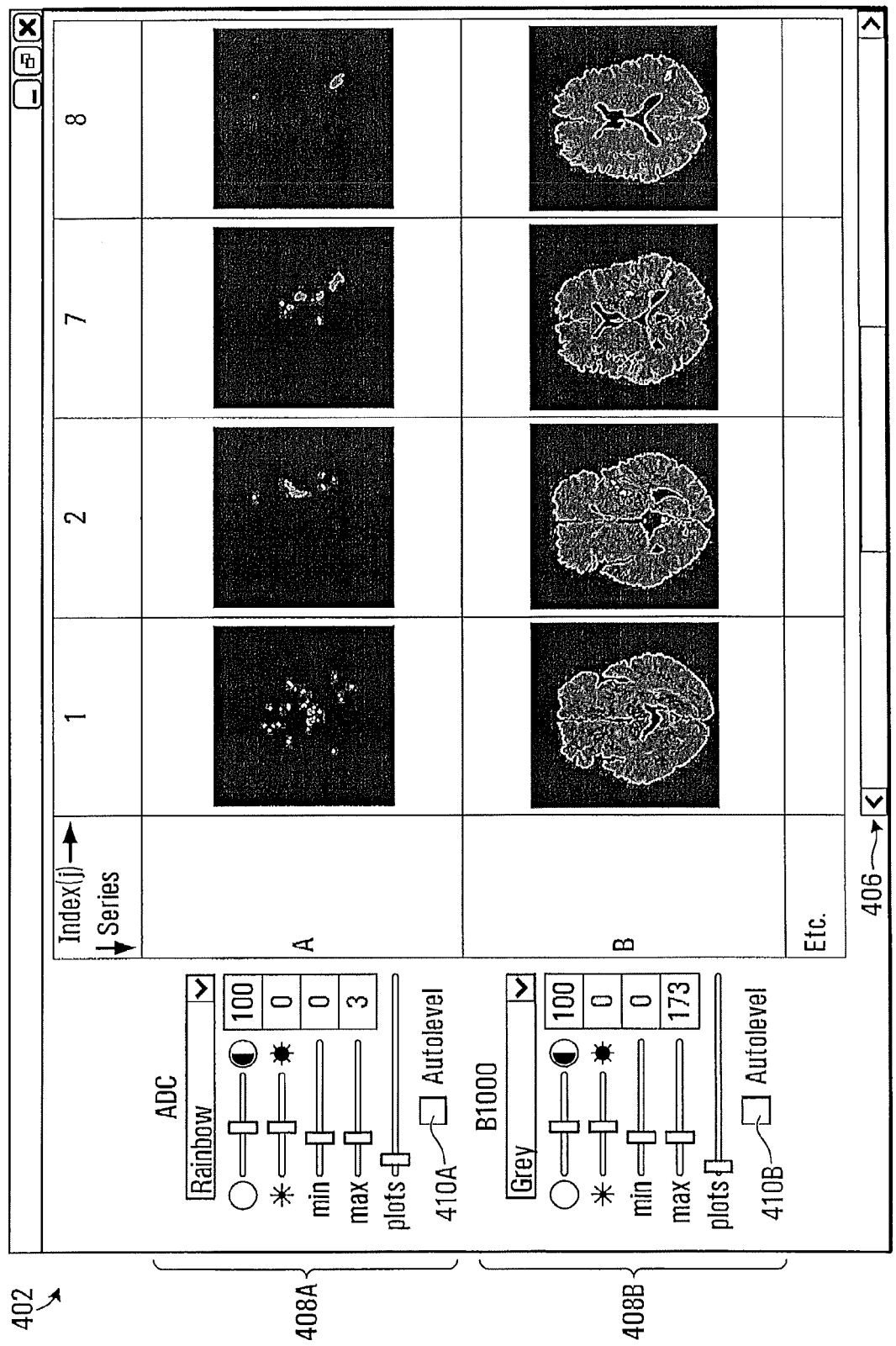
FIG. 4 is a screen shot illustrating a plurality of image series, each series having a plurality of images, where images in the same column are corresponding.

In a general sense, as shown in FIG. 4, a table 402 of M rows and N columns can be presented. It should be appreciated that M (i.e., the number of rows, that is, series) and N (i.e., the number of columns, that is, images per series) are variable, and can be varied by the user 114 by way of the input 108. In this case, M=2 and, specifically, images from series A and B are displayed. Also in this case, N=4 and, specifically, images having indexes 1, 2, 7 and 8 are displayed.

Also, scrolling functionality can be provided by, for example, a horizontal navigation bar 404, allowing the user 114 to manipulate which N indexes to display (the N indexes can be contiguous or individually selected). Similarly, scrolling functionality can be provided by, for example, a vertical navigation bar 406, allowing the user 114 to indicate from which M series the images for display will be taken from.

It should be appreciated that a key consideration is how to display the images in the table 402. Clearly, one option is to display the raw image content of the files 116, which may provide grayscale pixel values having an 8- or 16-bit dynamic range. However, it may be more beneficial to a clinician (who needs to view many images over a short period of time) to utilize a color scheme. When a color scheme is utilized, the value of a pixel is mapped to a color. Several standard color schemes can be provided, including rainbow, gray, etc., as well as customized color schemes. The same or different color schemes can be used for different image series. A touch-up panel 408A, 408B can be provided for each series whereby the color scheme can be selected for the particular image series. The touch-up panel 408A, 408B can also be used to manually apply other image processing features such as contrast and brightness.

It is also within the scope of the present invention to automatically optimize the color scheme selected for a particular series. Specifically, the color scheme has a range of colors that are mapped to pixel values. Without optimization, certain highly perceptible colors may not actually be rendered on the display device because they are mapped to pixel values that do not appear in the images in the particular series. In order to optimize the selected color scheme, an autolevel graphical element (such as a button) 410A, 410B allows the user 114 to select an "autolevel" function. The autolevel function adjusts the contrast and brightness for the images of the particular series, by constraining the values of the pixels in the images of the particular series to within m−s and m+s, where m is the average pixel value and s is the standard deviation of pixel values either (i) within each individual image or (ii) among all images of the series. Under the latter option, if the particular series is A, then a "red" pixel in image A(p) will correspond a value that is the same as the pixel value of a "red" pixel in image A(q) for any p and any q (provided of course that there are "red" pixels in images A(p) and A(q)).

Figure 7:
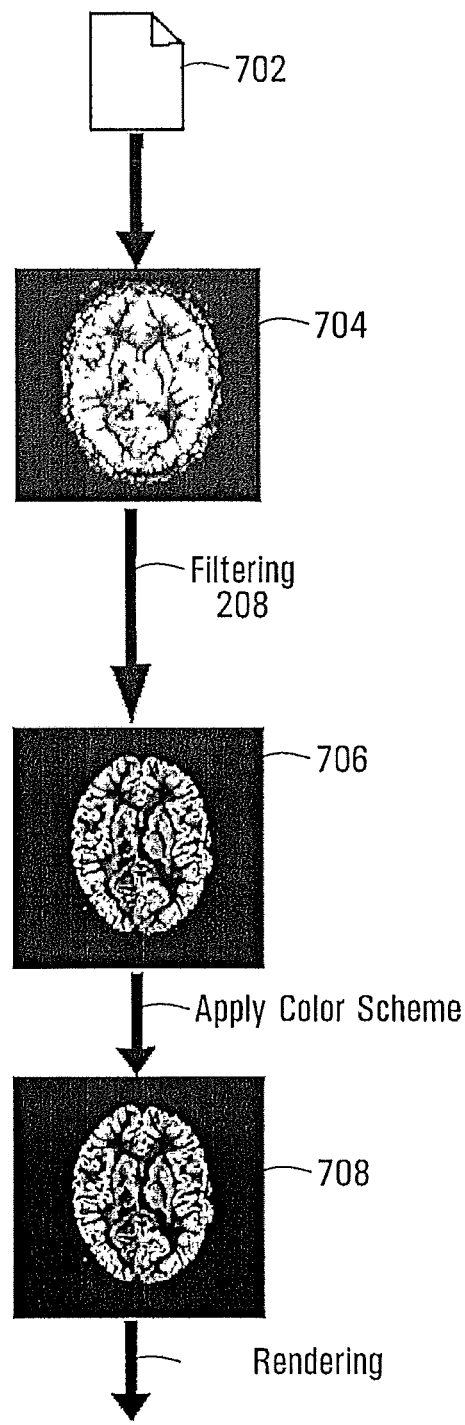
FIG. 7 shows steps in the transformation of an original image into a set of pixels that is ready to be rendered, in accordance with a non-limiting embodiment of the present invention.

It should be appreciated that activation of the touch-up panel 408A, 408B and/or the autolevel button 410A, 410B causes the computer 100 to vary the appearance of the images in the series as rendered on the display device without altering the original files 116. This can be achieved as follows. With reference to FIG. 7, an image of interest (e.g., a DICOM image) has pixel values that are stored in one of the files 116 in memory, say file 702. These pixel values are processed as per the registration step 202, thereby to yield a new set of pixel values that are stored in a second file 704 in memory. The contents of the second file 704 are copied into a third file 706. If applicable, the contents of the second file 704 are also used to generate a "segmentation mask" by the filtering step 208 (see below). The segmentation mask is then applied to the contents of the second file 704, thereby to yield a new set of pixel values which are stored in a third file 706 in memory. The contents of the third file 706 are used to calculate the optimized color scheme when the autolevel button 410A, 410B is activated. Then, the selected color scheme (whether optimized or not) as well as other functions (such as brightness and contrast, if applicable) are applied to the contents of the third file 706, which yields a new set of pixel values (which are high-resolution since they contain color information) that are stored in a fourth file 708 in memory. The fourth file 708 thus contains the actual color values that are rendered by the display device.

Step 208: Filtering

The step of filtering 208 is performed based on segmentation masks that can be created via the input 108. A segmentation mask defines a set of pixels to be eliminated from an image by bringing the value of those pixels captured by the segmentation mask to a baseline value (such as zero). A segmentation mask can be created according to various techniques, including but not limited to:
  a) using a source image, whose pixels are subjected to a validity interval [x,y], whereby pixels whose values fall outside the validity window are considered to form part of the segmentation mask;
  b) explicitly identifying a geometric figure, e.g., in free form or using a polygonal drawing tool, whereby pixels within the geometric figure are considered to form part of the segmentation mask; and
  c) based on a segmentation mask that has left isolated regions of pixels untouched, absorbing those regions into the segmentation mask.

Once created, the segmentation mask is applied to an image. Application of the segmentation mask brings the value of pixels captured by the segmentation mask to the baseline value, leaving the value of the other pixels intact. The result is the creation of a filtered image.

A segmentation mask can be applied to the image from which it was created, but also to images appearing in other series but corresponding to the image from which it was created (where correspondence is established in accordance with step 204 described above). Since corresponding images have the same pixel spacing, origin and orientation, the segmentation mask geometrically "fits" over all images corresponding to the image from which the segmentation mask was created. In some cases, the same segmentation mask can be used for images appearing at different axial slice heights, but it may be preferable to create different segmentation masks for different axial slice heights due to physiological dimensionality variations between adjacent axial slices.

Non-limiting examples of segmentation masks that can be created, along with some possible applications, are provided below:
  a) With reference to FIG. 6A, a segmentation mask 604 can be created using a source image 602 obtained from B1000-type DWI images, whose pixels are subjected to a validity interval. Application of the segmentation mask 604 can serve to isolate pixels representing the skull;
  b) With reference to FIG. 6B, a segmentation mask 614 can be created using a source image 612 obtained from CBV-type PWI images, whose pixels are subjected to a validity interval. Application of the segmentation mask 614 can serve to isolate pixels representing the patient's large vessels;
  c) With reference to FIG. 6C, a segmentation mask 624 can be created using a source image 622 obtained from ADC-type DWI images, whose pixels are subjected to a validity interval. Application of the segmentation mask 624 can serve to isolate pixels representing the cerebrospinal fluid (CSF). For more information, reference can be made to Imagerie de diffusion et de perfusion par résonance magnétique de l'encéphale, G. Cosnard et al., LOUVAIN MED, 118; 129-140, 1999;
  d) a segmentation mask created using a source image obtained from TTP-type PWI images or MTT-type perfusion-weighted images, whose pixels are subjected to a validity interval, can serve to isolate pixels representing areas affected by ischemic stroke; and
  e) a segmentation mask created using a source image obtained from CBF-type PWI images, whose pixels are subjected to a validity interval, can serve to isolate pixels whose values are aberrant.

Other applications of a segmentation mask are of course within the scope of the present invention.

It should be appreciated that some of the segmentation masks described above can be applied one after the other on the same image (or series of images), resulting in application of a "compound" segmentation mask, which has the features of removing noise, skull tissue, cerebrospinal fluid and large vessels, thus providing improved visibility of key features of interest in the cerebral tissue. Thus, multiple segmentation masks derived from multiple series can be applied to the same series. Similarly, the same original segmentation mask can be applied to images in multiple series, including the series containing the image from which the segmentation mask was derived.

Thus, for example, in the context of identifying the core ischemic zone, namely the tissue that has been irreversibly damaged due to oxygen deprivation, segmentation masks can be created to remove the skull and cerebrospinal fluid. Thereafter, the B1000 or ADC series can be displayed. From there, it may be possible to identify a region representing the core ischemic zone by creating and applying one or more further segmentation masks. A first such further segmentation mask can be used to remove pixels whose values fall below a threshold. A second such further segmentation mask can be created by absorbing remaining isolated pixels. Finally, the pixels that have not been captured by the compound segmentation mask represent areas of the cerebral tissue in the core ischemdc zone.

A next step is therefore to perform a volumetric computation.

Step 210: Volumetric Computation

The step of volumetric computation 210 is performed on a plurality of images of a given series. One specific volumetric computation of interest seeks to estimate the volume of the core ischemic zone. Specifically, having identified the core ischemic zone in each axial slice by a method such as that described above, the computer 100 can estimate the total volume of the core ischemic zone. This is basically a computation of the area of the identified region times inter-slice axial distance, but interpolated (e.g., in linear fashion) to account for variability in the area of the region of interest between neighbouring axial slices. In some embodiments, the computer 100 automatically performs this calculation for those images in the selected series (e.g., B1000 or ADC) where the region of interest appears. In other embodiments, the user 114 can select via the input 108 a specific set of images on which the volumetric computation will be performed, which can possibly reduce artifacts at the extreme axial slices. The output is thus a volume in an appropriate unit (e.g., CC).

Another volumetric computation can be effected for the ischemic penumbra in a similar fashion. In this case, the images under consideration can be PWI images that can allow isolation of a poorly irrigated area of the brain that is nevertheless salvageable/viable. Suitable image series are the TTP or MTT or Tmax series, for example, which can be filtered using a compound segmentation mask to arrive at a region on each image in the chosen series which represents the ischemic penumbra. The computer 100 can then effect a computation of the surface area of the region times inter-slice axial distance, but interpolated (e.g., in linear fashion) to account for variability in the area of the region of interest between axial slices. In some embodiments, the computer 100 automatically performs this calculation for those images in the selected series (e.g., TTP or MTT or Tmax) where the region of interest appears, whereas in other embodiments, the user 114 can select via the input 108 the images on which the volumetric computation will be performed, which can possibly reduce artifacts at the extreme axial slices. The output is thus a volume in an appropriate unit (e.g., CC).

It follows that the user 114 can have access to two important volumetric computations, namely that of the core ischemic zone and that of the ischemic penumbra. Then, based on the absolute and/or relative volumes of each, as well as other factors, the user 114 can be in a position to perform a more informed cost/benefit analysis regarding the option of administering a thrombolytic. This can be useful in both real-life and simulated environments. Further information on the clinical value of this approach can be found in *Optimal Definition for PWI/DWI Mismatch in Acute Ischemic Stroke Patients*, W Kakuda et al., *Journal of Cerebral Blood Flow & Metabolism* (2008), 1-5.

Of course, it should be appreciated that other ways of effecting a volumetric computation are within the scope of the present invention, and it should also be appreciated that computations can be performed to estimate the volume of other regions of interest of the imaged physiological structure.

In the above non-limiting embodiments of the present invention, particular emphasis has been placed on diagnosis and treatment of ischemic stroke, but it should be appreciated that embodiments of the present invention are applicable to other areas of neuromedicine (such as diagnosis and/or treatment of epilepsy, tumors, Alzheimer's, etc.) as well as potentially other areas of medicine in general. In each of these contexts, the biological images of particular significance may be different, but the principles set forth herein are clearly applicable thereto.

Those skilled in the art will also appreciate that inputs received from the user 114 can be recorded (and restored) by the computer 100 so as to serve for traceability and training purposes. More specifically, the computer 100 can record the values of the pixels that were displayed (based on user selections of contrast, brightness, color scheme, etc.), the validity intervals [x,y] used in the creation segmentation masks, the various parameters of other segmentation masks used for isolating the core ischemic zone and the ischemic penumbra, the parameters used to calculate the perfusion images, and so on.

While specific embodiments of the present invention have been described and illustrated, it will be apparent to those skilled in the art that numerous modifications and variations can be made without departing from the scope of the invention as defined in the appended claims.

What is claimed is:

1. A method for processing images in a system having a computer and a display device, the method comprising:
    obtaining a plurality of series of biological images by the computer, wherein at least one series is in a first biological class and at least one other series is in a second biological class different from the first biological class, and wherein certain images in any series correspond to certain images in the other series;
    performing a registration process, by the computer, to align pixels of certain images in one series with the corresponding pixels of certain images in the other series;
    creating, by the computer, a segmentation mask for a selected image in a series in the first biological class whose pixels are aligned in accordance with the registration process, wherein the segmentation mask defines a set of pixels to be eliminated from that selected image; and
    applying, by the computer, the segmentation mask to a corresponding image in another series in the second biological class whose pixels are aligned in accordance with the registration process, to eliminate corresponding pixels of the image in the other series; and
    displaying, on the display device, the image from the other series whose pixels were eliminated by the segmentation mask.

2. The method of claim 1, wherein the elimination of a pixel comprises setting a value of the pixel to a baseline value if the pixel is within the set defined by the segmentation mask.

3. The method of claim 1, wherein:
    each of the selected images in a series comprises an array of pixels or voxels having respective values; and creating the segmentation mask for an image in a series comprises:
comparing the value of each pixel or voxel in the particular image to a range; and
adding the pixel or voxel to the set of pixels defined by the segmentation mask if the value of the pixel or voxel is outside the range.

4. The method of claim 1, wherein:
each selected image in a series comprises an array of pixels or voxels having respective values; and
creating the segmentation mask for an image in a series comprises specifying a geometric figure based on received input.

5. The method of claim 1, wherein:
each selected image comprises an array of pixels or voxels having respective values; and
creating a segmentation mask comprises adding a region of pixels or voxels left isolated by creation of a previous segmentation mask.

6. The method of claim 1, further comprising:
selecting a set of images in the other series on which to effect a volumetric computation; and
effecting a volumetric computation of a region represented by pixels that have not been eliminated, based on the images.

7. The method of claim 6, wherein effecting the volumetric computation comprises estimating the volume of interest based on:
an area of the region exhibited by each image in the set; and
an inter-slice distance between adjacent images in the set.

8. The method of claim 6, wherein the volumetric computation represents an estimate of a volume of a core ischemia zone.

9. The method of claim 6, wherein the volumetric computation represents an estimate of a volume of an ischemia penumbra zone.

10. The method of claim 6, further comprising displaying the volumetric computation.

11. The method of claim 1 wherein, following application of a respective segmentation mask to a given image in a series, the given image exhibits a region corresponding to a cross-section of a volume of interest spanning the images in the series.

12. The method of claim 1, wherein a series is diffusion-weighted or perfusion-weighted.

13. The method of claim 12, wherein the series in the first biological class is one of diffusion-weighted or perfusion-weighted, and the other series in the second biological class is the other of diffusion-weighted or perfusion-weighted.

14. The method of claim 12, wherein a diffusion-weighted series comprises a B1000 series or an Apparent Diffusion Coefficient series.

15. The method of claim 1, further comprising, prior to the obtaining, establishing a correspondence between certain images in a series and certain images in another series.

16. The method of claim 15, wherein:
each image is associated with a respective axial slice; and
the establishing comprises:
initializing a threshold slice height difference;
attempting to identify a pair of corresponding images such that:
the pair of corresponding images includes one image from each of the series; and
the images in each pair are associated with respective slice heights differing by no more than the threshold slice height difference;
increasing the threshold slice height difference; and
repeating the attempting and the increasing until the threshold slice height difference reaches a maximum threshold slice height difference.

17. The method of claim 16, further comprising:
for each image in the series that has not been paired by the repeating, pairing the image with a blank image.

18. The method of claim 1, wherein the registering of certain images in one series and certain images in another series is carried out within a common frame of reference.

19. The method of claim 18, wherein registering a particular image within a common frame of reference comprises one or more of zooming, rotating, and translating the image relative to an original frame of reference.

20. The method of claim 1, wherein the images are magnetic resonance images and the images in the series in the first biological class and the images in the other series in the second biological class originate from respectively different radiological modalities.

21. The method of claim 1, wherein the set of pixels defined by the segmentation mask isolate a component of the selected image from other components of the selected image.

22. A non-transitory computer-readable storage medium having computer-executable instructions stored thereon for processing images, the instructions comprising:
instructions for obtaining a plurality of series of biological images including a first series in a first biological class and a second series in a second biological class different from the first biological class, wherein certain images in any series correspond to certain images in other series;
instructions for registering images to align pixels of certain images in one series with the corresponding pixels of certain images in the other series;
instructions for receiving selections of one or more images from the first series whose pixels have been aligned;
instructions for creating a respective segmentation mask for each of the selected one or more images in the first series, wherein the segmentation mask defines a set of pixels to be eliminated from that selected image;
instructions for applying the respective segmentation mask to a corresponding image in the second series whose pixels have been aligned, to eliminate corresponding pixels of the image in the other series, and
instructions for displaying the image from the other series whose pixels were eliminated by the segmentation mask.

23. The computer-readable storage medium of claim 22, the instructions further comprising:
instructions for setting a value of a pixel to a baseline value in response to determining that the pixel is in the set defined by the segmentation mask.

24. The computer-readable storage medium of claim 22, wherein a series is diffusion-weighted or perfusion-weighted.

25. The computer-readable storage medium of claim 24, wherein the first series is one of diffusion-weighted or perfusion-weighted, and the second series is the other of diffusion-weighted or perfusion-weighted.

26. The computer-readable storage medium of claim 22, wherein the first series originates from a first radiological modality and the second series originates from a second radiological modality different from the first radiological modality.

27. A method for processing images in a system having a computer and a display device, the method comprising:
obtaining a plurality of series of biological images by the computer, wherein the images in at least one series contain a first type of biological information, and the images in at least one other series contain a second type of biological information different from the first type of biological information, and wherein certain images in any series correspond to certain images in other series;

performing a registration process, by the computer, to align pixels of certain images in one series with the corresponding pixels of certain images in the other series;

creating, in the computer, a segmentation mask for a selected image in a series containing the first type of biological information whose pixels are aligned in accordance with the registration process, wherein the segmentation mask defines a set of pixels to be eliminated from the selected image;

applying, via the computer, the segmentation mask to a corresponding image in another series containing the second type of biological information whose pixels are aligned in accordance with the registration process, to eliminate corresponding pixels of the image in the other series; and displaying, on the display device, the image from the other series whose pixels were eliminated by the segmentation mask.

28. The method of claim 27, wherein the elimination of a pixel comprises setting a value of the pixel to a baseline value if the pixel is in the set defined by the segmentation mask.

29. The method of claim 27, wherein the set of pixels defined by the segmentation mask isolate a component of the selected image from other components of the selected image.

30. A non-transitory computer-readable storage medium having computer-executable instructions stored thereon for processing images, the instructions comprising:
    instructions for obtaining a plurality of series of biological images including a first series whose images contain a first type of biological information, and a second series whose images contain a second type of biological information different from the first type of biological information, wherein certain images in any series correspond to certain images in other series;
    instructions for registering images to align pixels of certain images in one series with the corresponding pixels of certain images in the other series;
    instructions for receiving selections of one or more images from the first series whose pixels have been aligned;
    instructions for creating a respective segmentation mask for each of the selected one or more images in the first series, wherein a segmentation mask defines a set of pixels to be eliminated from the selected image;
    instructions for applying the respective segmentation mask to a corresponding image in the second series whose pixels have been aligned, to eliminate corresponding pixels of the image in the other series, and
    instructions for displaying the image from the other series whose pixels were eliminated by the segmentation mask.

31. The computer-readable storage medium of claim 30, wherein the instructions for applying further comprise setting a value of a pixel to a baseline value if a determination is made that the pixel is in the set defined by the segmentation mask.

32. The computer-readable storage medium of claim 30, wherein the set of pixels defined by the segmentation mask isolate a component of the selected image from other components of the selected image.

33. A system comprising:
    means for obtaining a plurality of series of biological images including a first series whose images contain a first type of biological information, and a second series whose images contain a second type of biological information different from the first type of biological information, wherein certain images in the first series and certain images in the second series are corresponding;
    means for registering images to align pixels of certain images in one series with the corresponding pixels of certain images in the other series;
    means for creating a respective segmentation mask for each selected image in said first series whose pixels have been aligned, wherein the segmentation defines a set of pixels to be eliminated from the selected image;
    means for applying said respective segmentation mask to the corresponding image in the second series whose pixels have been aligned, to eliminate corresponding pixels of the image in the other series; and,
    means for displaying the image from the other series whose pixels were eliminated by the segmentation mask.

34. The system of claim 33, wherein the means for applying includes means for setting a value of a pixel to a baseline value if a determination is made that the pixel is within the set defined by the segmentation mask.

35. The method of claim 33, wherein the set of pixels defined by the segmentation mask isolate a component of the selected image from other components of the selected image.

36. A method for processing a plurality of series of biological images obtained from a patient in a system having a computer and a display device, comprising:
    obtaining a plurality of series of biological images by the computer, including a first series whose images contain a first type of biological information, and a second series whose images contain a second type of biological information different from the first type of biological information, wherein certain images in any series correspond to certain images in other series;
    performing a registration process by the computer, to align pixels of certain images in said first series with corresponding pixels of certain images in said second series;
    creating, by the computer, a segmentation mask for a selected image in said first series;
    applying, by the computer, said segmentation mask to a corresponding image in said second series, and obtaining a set of images that exhibit a region corresponding to a cross-section of a volume of interest spanning the corresponding images;
    effecting a volumetric computation in the computer, based on said set of images, and
    displaying, on the display device, an image from the set of images.

37. The method of claim 36, wherein effecting the volumetric computation comprises estimating the volume of interest based on:
    an area of the region exhibited by each image in the set; and
    an inter-slice distance between adjacent images in the set.

38. The method of claim 36, wherein the volumetric computation represents an estimate of a volume of a core ischemia zone.

39. The method of claim 36, wherein the volumetric computation represents an estimate of a volume of an ischemia penumbra zone.

40. The method of claim 36, further comprising displaying said volumetric computation.

* * * * *